United States Patent [19]

Carceller et al.

[11] Patent Number: 5,407,941
[45] Date of Patent: Apr. 18, 1995

[54] 8-CHLORO-11-[1-[(5-METHYL-3-PYRIDYL)-METHYL]-4-PIPERIDYLIDEN]-6,11-DIHYDRO-5H-BENZO[5,6]CYCLOHEPTA[1,2-B]PYRIDINE

[75] Inventors: Elena Carceller; Nûria Recasens; Carmen Almansa; Javier Bartrolí; Manel Merlos; Marta Giral; Julián Garcia-Rafanell; Javier Forn, all of Barcelona, Spain

[73] Assignee: J. Uriach & Cia. S.A., Spain

[21] Appl. No.: 61,720

[22] Filed: May 17, 1993

[30] Foreign Application Priority Data

May 22, 1992 [ES] Spain ..................... 9201054

[51] Int. Cl.⁶ .................. A61K 31/435; C07D 401/02
[52] U.S. Cl. ........................ 514/290; 546/93
[58] Field of Search ................... 514/290; 546/93

[56] References Cited

U.S. PATENT DOCUMENTS 4,282,233  8/1981  Vilani .
5,089,496  2/1992  Piwioski et al. ............. 514/253

FOREIGN PATENT DOCUMENTS 0152897  8/1985  European Pat. Off. .
0371805  6/1990  European Pat. Off. .
0396083  11/1990  European Pat. Off. .
8803138  5/1988  WIPO .
89/10363  11/1989  WIPO .
9013548  11/1990  WIPO .
9200293  1/1992  WIPO .
92/14734  9/1992  WIPO .

OTHER PUBLICATIONS

Schumacher et al., *J. Org. Chem.*, 1989, 54, 2242–2244.
Bruneau et al., *J. Med. Chem.*, 1991, 34, 1028–1036.
Rebek et al., *J. Am. Chem. Soc.*, 1985, 107, 7487–7493.
Born, *Proceedings of the Physiological Society*, Mar. 1962, vol. 23–24, 67 P.
Young et al., *Prostaglandins*, 1985, 30, 545–551.

*Primary Examiner*—Johann Richter
*Assistant Examiner*—Michael B. Hydern
*Attorney, Agent, or Firm*—Rothwell, Figg, Ernst & Kurz

[57] ABSTRACT

The present invention relates to 8-chloro-11-[1-[(5-methyl-3-pyridyl)methyl]-4-piperidyliden]-6,11-dihydro-5H-benzo[5,6]cyclohepta[1,2-b]pyridine, to a process for its preparation and to pharmaceutical compositions containing it. This compound is a dual PAF antagonist and antihistamine.

6 Claims, No Drawings

8-CHLORO-11-[1-[(5-METHYL-3-PYRIDYL)METHYL]-4-PIPERIDYLIDEN]-6,11-DIHYDRO-5H-BENZO[5,6]CYCLOHEPTA[1,2-B]PYRIDINE

The present invention relates to 8-chloro-11-[1-[(5-methyl-3-pyridyl)methyl]-4-piperidyliden]-6,11-dihydro-5H-benzo[5,6]cyclohepta[1,2-b]pyridine, which is a potent PAF antagonist and antihistamine. The invention also relates to a process for its production, to the pharmaceutical compositions containing it and to its use in the treatment of the diseases in which PAF and/or histamine are involved.

WO 88/03138 discloses certain benzo[5,6]cyclohepta[1,2-b]pyridine derivatives of formula

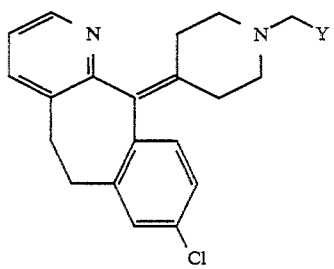

wherein Y represents —COOR$^1$, —E—COOR$^1$ or —E—OR$^2$ where E is alkanediyl which may be substituted with —OR$^1$, —SR$^1$, —N(R$^1$)$_2$ or —D, where R$^1$ is hydrogen, alkyl or aryl; R$^2$ represents R$^1$, —(CH$_2$)$_m$OR$^1$ or —(CH$_2$)$_q$CO$_2$R$^1$, being R$^1$ as above defined, m is 1, 2, 3 or 4 and q is 0, 1, 2, 3 or 4; and D represents certain aromatic heterocycles. However, no mention to Y being a heterocycle is made.

WO 92/00293 discloses novel compounds with the above general formula wherein Y represents a pyridine or a N-oxide pyridine group optionally substituted with R$^7$, R$^8$ and R$^9$.

R$^7$, R$^8$ and R$^9$ each independently represents hydrogen, halogen, —CF$_3$, —OR$^{11}$, —C(=O)R$^{11}$, —SR$^{11}$, —S(O)$_e$R$^{13}$ where e is 1 or 2, —N(R$^{11}$)$_2$, —NO$_2$, —OC(=O)R$^{11}$, —CO$_2$R$^{11}$, CN, —OCO$_2$R$^{13}$, NR$^{11}$C(=O)R$^{11}$, alkyl, aryl, alkenyl or alkynyl, which alkyl group may be substituted with —OR$^{11}$, —SR$^{11}$, —N(R$^{11}$)$_2$ or —CO$_2$R$^{11}$ and which alkenyl group may be substituted with halogen, —OR$^{13}$ or —CO$_2$R$^{11}$; each R$^{11}$ independently represents hydrogen, alkyl or aryl and each R$^{13}$ independently represents alkyl or aryl. From the compounds included in this general formula, only two of them, namely 8-chloro-11-[1-(4-pyridylmethyl)-4-piperidyliden]-6,11-dihydro-5H-benzo[5,6]cyclohepta[1,2-b]pyridine and 8-chloro-11-[1-(N-oxide-4-pyridylmethyl)-4-piperidyliden]-6,11-dihydro-5H-benzo[5,6]cyclohepta[1,2-b]pyridine, were actually prepared.

Considering that the PAF antagonist and antihistaminic activity of these compounds could depend to a great extent on the appropriate selection of the position of the pyridinic nitrogen and on the nature and position of the substituents in the pyridine ring present in the radical Y, we have prepared and tested a series of 3-pyridylmethyl derivatives of 8-chloro-11-(4-pyperidyliden)-6,11-dihydro-5H-benzo[5,6]cyclohepta[1,2-b]pyridine (the number beside each formula corresponds to the example in which their preparaton is described):

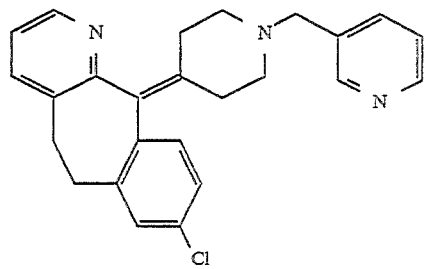

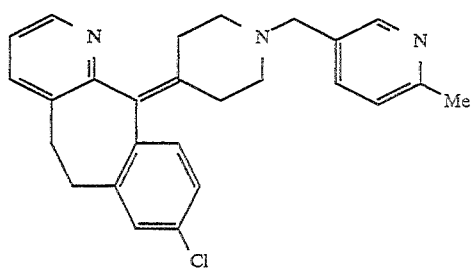

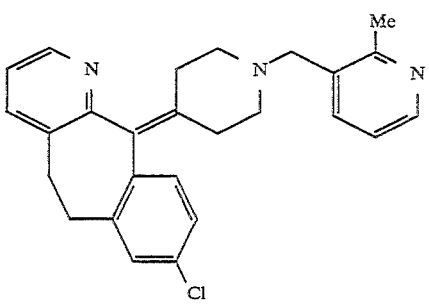

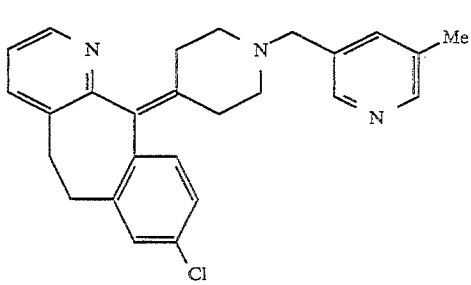

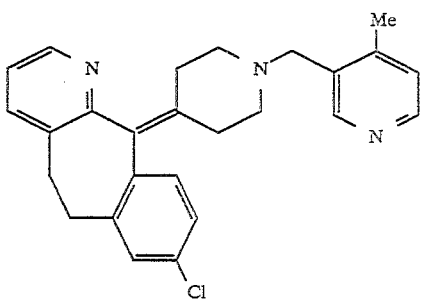

-continued

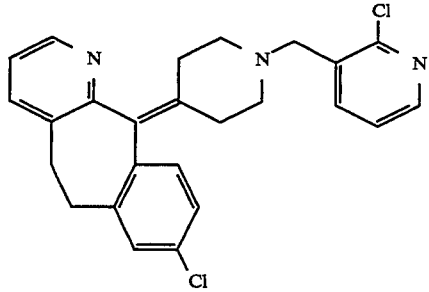
6

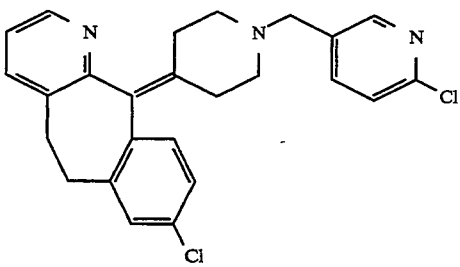
7

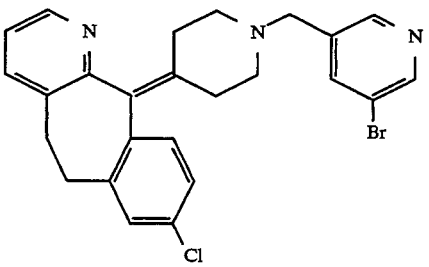
8

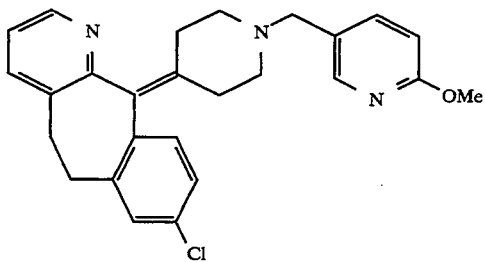
9

Surprisingly, we have found that the compound 8-chloro-11-[1-[(5-methyl-3-pyridyl)methyl]-4-piperidyliden]-6,11-dihydro-5H-benzo[5,6]cyclohepta[1,2-b]pyridine (or compound No. 4) exhibits a dual activity as PAF antagonist and antihistamine superior to the activity of the above mentioned Prior Art compounds and superior also to the activity of the other 3-pyridylmethyl derivatives prepared by us. Thus, both the election of the position of the pyridinic nitrogen and the election of the-substituent of the pyridine and its position in the pyridinic ring not only are not obvious but, furthermore, they are determining factors for the presence of PAF antagonist and antihistaminic activity in this class of compounds.

Therefore, the present invention is directed to the new compound 8-chloro-11-[1-[(5-methyl-3-pyridyl)-methyl]-4-piperidyliden]-6,11-dihydro-5H-benzo[5,6-]cyclohepta[1,2-b]pyridine (4) and the pharmaceutically acceptable salts and solvates thereof.

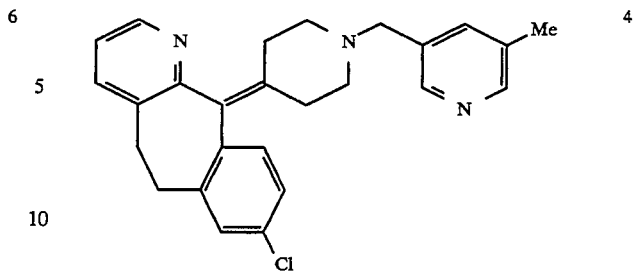
4

The invention also provides a pharmaceutical composition which comprises an effective amount of 8-chloro-11-[1-[(5-methyl-3-pyridyl)methyl]-4-piperidyliden]-6,11-dihydro-5H-benzo[5,6]cyclohepta[1,2-b]pyridine (4) or a pharmaceutically acceptable salt or solvate thereof in combination with a pharmaceutically acceptable excipient.

The invention further provides the use of 8-chloro-11-[1-[(5-methyl-3-pyridyl)methyl]-4-piperidyliden]-6,11-dihydro-5H-benzo[5,6]cyclohepta[1,2-b]pyridine (4) or a pharmaceutically acceptable salt or solvate thereof for the treatment and/or prevention of the diseases in which PAF and/or histamine are involved.

The invention is further directed to a process for preparing 8-chloro-11-(1-[(5-methyl-3-pyridyl)methyl]-4-piperidyliden)-6,11-dihydro-5H-benzo[5,6]cyclohepta[1,2-b]pyridine (4) which comprises reacting a compound of formula II

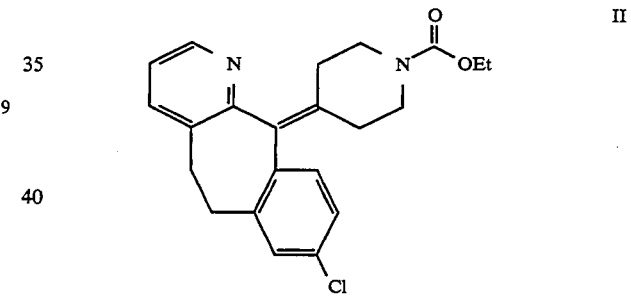
II with trimethylsilyl iodide in a suitable solvent such as chloroform, to give a compound of formula III,

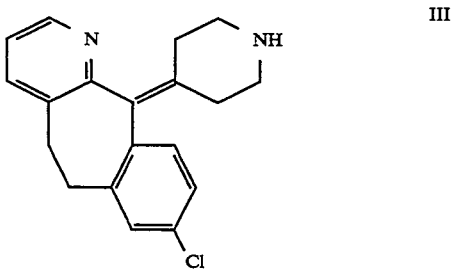
III which is then allowed to react with a compound of formula XCH$_2$R, wherein R is a 5-methyl-3-pyridyl group and X represents a halogen atom, such as chlorine or bromine, in the presence of a proton scavenger base such as triethylamine or pyridine in a suitable solvent such as carbon tetrachloride, dichloromethane or chloroform; or alternatively, III is allowed to react with 5-methylnicotinic acid or an equivalent acylating reagent in a manner known per se in organic chemistry, and subsequently reducing the resulting amide with a reducing agent such as LiAlH$_4$ in a suitable solvent such as tetrahydrofuran;

and optionally, reacting compound 4 with an acid to give its corresponding acid addition salt.

The compound 8-chloro-11-[1-[(5-methyl-3-pyridyl)-methyl]-4-piperidyliden]-6,11-dihydro-5H-benzo[5,6-]cyclohepta[1,2-b]pyridine (4) contains basic nitrogen atoms and, consequently, it can form salts, which form also part of the present invention. There is no limitation on the nature of these salts, provided that, when used for therapeutic purposes, they are pharmaceutically aceptable, which, as is well known in the art, means that they do not have reduced activity (or unacceptable reduced activity) or increased toxicity (or unacceptable increased toxicity) compared with the free compound. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid, citric acid; and other mineral and carboxylic acids well known to those skilled in the art. The salts are prepared by contacting the free base form with a sufficient amount of the desired acid to produce a salt in the conventional manner. The free base form differs from its salt forms somewhat in certain physical properties, such as solubility in polar solvents, but they are equivalent for purposes of the invention.

The compound object of the present invention can exist in unsolvated as well as solvated forms, including hydrated forms. In general, the solvated forms, with pharmaceutically acceptable solvents such as water, ethanol and the like are equivalent to the unsolvated form for purposes of the invention.

The compound of the present invention, i.e. 8-chloro-11-[1-[(5-methyl-3-pyridyl)methyl]-4-piperidyliden]-6,11-dihydro-5H-benzo[5,6]cyclohepta[1,2-b]pyridine (4), and the other 3-pyridylmethyl derivatives of 8-chloro-11-(4-piperidyliden)-6,11-dihydro-5H-benzo[5,6]cyclohepta[1,2-b]pyridine we have prepared can be represented by the following general formula I:

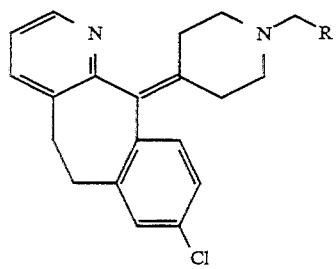

wherein R represents a 3-pyridyl group which may be optionally substituted with a halogen atom, or with a C$_{1-4}$ alkyl or C$_{1-4}$ alkoxy group and can be prepared by the following processes.

Compounds of formula I can be prepared by reaction of amine III with a compound of general formula XCH$_2$R (IV, wherein R has the above defined meaning and X is a halogen atom, such as chlorine or bromine) in the presence of a proton scavenger base, such as triethylamine or pyridine, in a suitable solvent, such as carbon tetrachloride, dichloromethane or chloroform. The reaction is carried out at a temperature between 0° C. and that of the boiling point of the solvent and during a reaction time from 6 to 48 h.

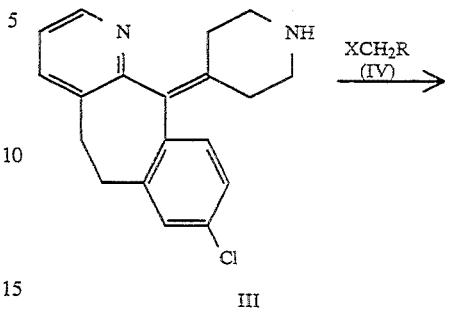

Alternatively, compounds of general formula I can be obtained by reduction of the amido moiety of a compound of general formula VI. Although in principle any reducing agent of amido groups which is compatible with the reaction conditions could be employed, such as BH$_3$ or POCl$_3$/NaBH$_4$, we have found that the reaction works conveniently using LiAlH$_4$ as reducing agent and tetrahydrofuran as solvent.

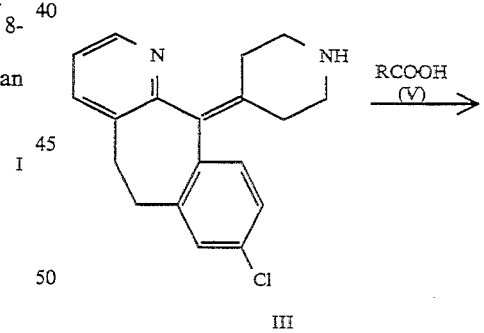

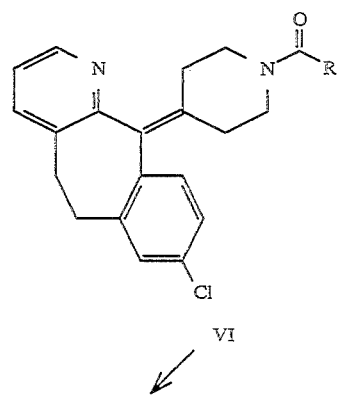

-continued

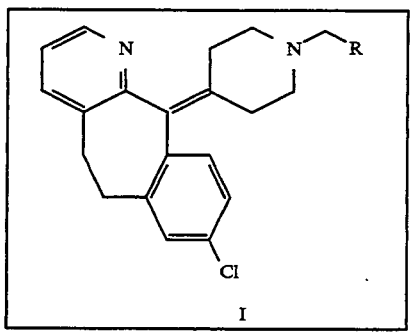

I

The amides of formula VI are prepared by a dehydration procedure between amine of formula III and carboxylic acids of general formula RCOOH (V, wherein R has the previously defined meaning). This dehydration process can be carried out by using any conventional reaction of amide bond formation, such as the following processes:

a) By reaction between amine III and an acid of general formula RCOOH (V) in the presence of dicyclohexylcarbodiimide and 1-hydroxybenzotriazole in a suitable solvent; as examples of suitable solvents can be mentioned dioxane, tetrahydrofuran, acetonitrile, chloroform and N,N-dimethylformamide. The reaction is performed at a temperature ranging from 0° to 60° C. during a period of time from 6 to 24 hours.

b) By reaction between amine III with an acid chloride or anhydride derived from an acid of general formula RCOOH (V) in the presence of a proton scavenger amine, such as pyridine or triethylamine, in a suitable solvent such as carbon tetrachloride, dichloromethane or chloroform, or else the same proton scavenger amine can be used as solvent. The reaction is carried out at a temperature between 0° C. and that of the boiling point of the solvent, during a period of time from 6 to 24 hours. The compounds thus obtained are purified by flash chromatography or recrystallization.

The amine of formula III is prepared from loratadine (II), which is a known compound (see, for example, Schumacher et al., *J. Org. Chem.*, 1989, 54, 2242-2244), by treatment with trimethylsilyl iodide in a suitable solvent such as chlorofom at a temperature between 55° and 60° C. and during a reaction time from 6 to 24 h.

Alkyl halides of general formula $XCH_2R$ (IV) either have been widely described in the literature or else can be prepared following analogous methods to those described (see, for example: Bruneau et al., *J. Med. Chem.*, 1991, 34, 1028-1036 and the references cited therein, and Rebek et al., *J. Am. Chem. Soc.*, 1985, 107, 7487-7493).

Acids of general formula RCOOH (V) are either commercial, or widely described in the literature or can be prepared by methods similar to those described, starting from commercially available products.

The compound of the present invention, this is 8-chloro-11-[1-[(5-methyl-3-pyridyl)methyl]-4-piperidyliden]-6,11-dihydro-5H-benzo[5,6]cyclohepta[1,2-b]pyridine (4), possesses PAF and histamine antagonistic properties. Therefore, it is useful in the treatment of diseases where PAF and/or histamine are involved. Compound (4), being a potent PAF antagonist, is useful as a preventive and therapeutic drug for the treatment of circulatory diseases caused by PAF, such as thrombosis, cerebral apoplexy (e.g. cerebral hemorrhage, cerebral thrombosis), myocardial infarction, angina pectoris, thrombotic phlebitis, thrombocitopenic purple, nephritis (e.g. glomerular nephritis), diabetic nephrosis, ischemia and shock states (e.g. septic shock observed after severe infection or postoperatively, intravascular agglutination syndrome caused by endotoxin, anaphylactic shock, hemorrhagic shock, myocardial ischemia); gastrointestinal tract diseases where PAF is involved (e.g. gastric ulcer, inflammatory bowel disease); diseases related to allergy and inflammation (e.g. asthma, dermatitis, urticaria, arthritis, psoriasis); pneumonia; rejection due to increased PAF production after implantations of organs; and postoperative organodysfunction (e.g. in heart, liver and kidney). It can also be used for contraception of female mammals by suppressing cell division and/or ovoimplantation on the uterus, in the treatment of endometriosis and in the prevention or treatment of hyperendothelinemia induced by excess secretion of endothelin. Being a potent antihistamine, compound 4 is useful as preventive and therapeutic drug for the treatment of diseases such as allergy (e.g. rhinitis, conjunctivitis, pruritus, urticaria, dermatitis), asthma and anaphylactic shock. Being a dual PAF and histamine antagonist, compound 4 is particularly useful for the treatment of complex pathologies such as asthma and allergic disorders of diverse ethiology in which a wide range of cellular mediators such as PAF and histamine are involved.

The following pharmacological tests explain the activity of 8-chloro-11-[1-[(5-methyl-3-pyridyl)methyl]-4-piperidyliden]-6,11-dihydro-5H-benzo[5,6]cyclohepta[1,2-b]pyridine (4) in more detail.

PHARMACOLOGICAL TEST 1

Inhibition of Platelet Aggregation Induced by PAF

The blood is obtained by cardiac puncture of male New Zealand albino rabbits (b.w. 2-2.5 Kg) and coagulation is prevented by adding 1 part of 3.16% sodium citrate dihydrate in 9 parts of blood. The platelet rich plasma (PRP) is prepared by blood centrifugation at 250×g for 10 min. at 4° C. and it is diluted with platelet poor plasma (PPP) obtained by additional centrifugation at 3000×g for 10 min. The amount of platelets is adjusted to $3 \times 10^{-5}/mm^3$. The platelet aggregation induced by PAF ($C_{18}$, prepared in our laboratory) (16 nM, final) is determined by the Born nephelometric technique (*J. Physiol.*, 1962, 162, 67) using an aggregometer Chrono-log 500. The activities of the inhibitors are expressed as $IC_{50}$ values, that is to say the concentration of the drug needed to inhibit the platelet aggregation in a 50%. The results are shown in table I below.

PHARMACOLOGICAL TEST 2

Inhibition of the Hypotensive Effect Induced by PAF in Normotense Rats

Male Sprage Dawley rats (b.w. 180-220 g) anesthetized with sodium pentobarbital (50 mg/Kg, i.p. 1 mL/100 g) are used. In order to measure the average arterial pressure, a polyethylene catheter is introduced into the carotid artery. The arterial pressure is recorded with the help of a transducer connected with a R611 Beckman polygraph. The test compounds are administered through the femoral vein 3 min. before the injection of PAF (0.5 mcg/Kg, i.v.). Table I shows the inhibition of the hypotension induced by PAF of the different compounds, expressed as the $ID_{50}$ values, that is to say, the amount of compound by weight of animal (dose) needed to inhibit the hypotension induced by PAF in a 50%. Results are shown in table I below.

PHARMACOLOGICAL TEST 3

Mortality Induced by PAF in Mice (P.O.)

This test was performed according to the procedure described by Young et al. (*Prostaglandins*, 1985, 30, 545-551). Groups of 10 Swiss mice weighing from 22 to 26 g were used. 100 mcg/kg of PAF-$C_{18}$ and 1 mg/kg of propanolol were administered through a lateral tail vein 1 h after the oral administration of the compounds to be tested (0.2 mL/10 g). Animals were examined 2 h after the injection of PAF. The percentage of the inhibition of the mortality induced by PAF was determined for all test compounds in comparison with the control group. The results are expressed as $ID_{50}$ values, that is to say, the amount of compound by weight of animal (dose) needed to inhibit the mortality induced by PAF in a 50%. Results are shown in table I below.

PHARMACOLOGICAL TEST 4

Antihistamine Activity in Guinea-Pig Ileum

This test was performed according to the method of Magnus. Male Dunkin-Hartley guinea pigs (b.w. 300-350 g), fasted overnight, were used. Animals were stunned, the abdomen was opened and 4 cm long ileum sections were cut. The sections were placed in a Petri dish containing Tyrode's solution at 37° C. and continuously bubbled with carbogen. The ileum fragments were washed with Tyrode's solution and then were transferred to an organ bath. Ileum contraction was measured using an isometric transducer. The initial load was 1 g. After a stabilization period of 20 min in which the organ is immersed in Tyrode's solution at 37° C. continuously bubbled with carbogen, non cumulative stimuli with submaximal doses of histamine ($5 \times 10^{-7}$M) were given. The contraction in absence or presence (5 min. preincubation time) of the test compounds was recorded. The activities of the antagonists are expressed as $IC_{50}$ values, that is to say the concentration of the drug required to inhibit histamine-induced contraction in a 50%. The results are shown in table I below.

In table I, the numbers in the compound column refer to the following compounds:

(A) Numbers 1 to 9 correspond to the compounds prepared in the examples of the same number and whose formulae are depicted in page 3 of the present specification;

(B) Compound 11 represents

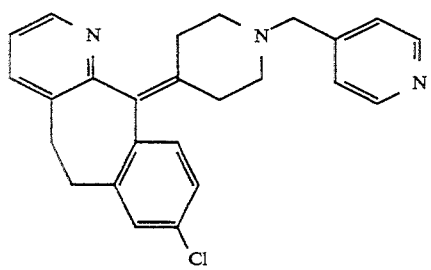

(C) Compound 12 represents

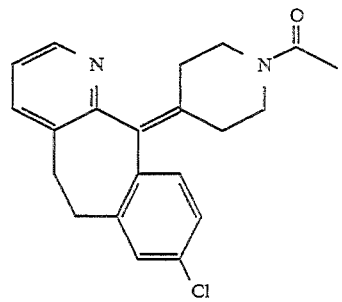

(D) Compound 13 represents

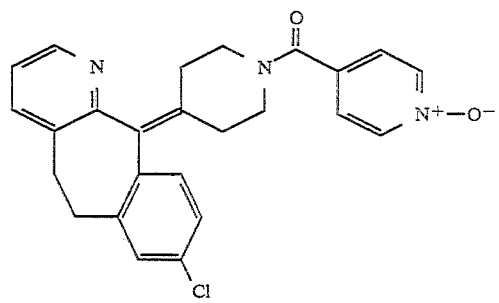

(E) Compound 14 represents

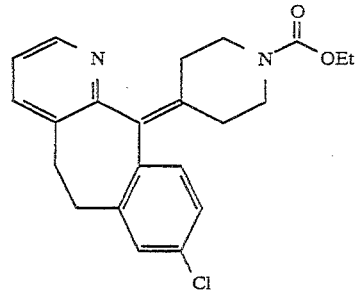

TABLE I

| | PAF ANTAGONISM | | | ANTIHISTA-MINIC ACTIVITY |
|---|---|---|---|---|
| | in vitro TEST 1 Plat aggreg. $IC_{50}$ (μM) | in vivo TEST 2 Art. p. $ID_{50}$ (mg/kg) iv | in vivo TEST 3 Mort. $ID_{50}$ (mg/kg) po | in vitro TEST 4 AntiH$_1$ act. ileum $IC_{50}$ (μM) |
| Compounds | | | | |
| 1 | 4.0 | >5 | 30 | 0.16 |
| 2 | 9.0 | >5 | 30 | 0.037 |
| 3 | 13 | >5 | >30 | 0.27 |
| 4 | 3.2 | 0.44 | 1.9 | 0.0043 |
| 5 | 15 | >5 | 10-30 | 0.035 |
| 6 | >100 | >5 | >30 | 0.35 |
| 7 | >100 | >5 | 20-30 | |
| 8 | 0.72 | >5 | <30 | 0.28 |
| 9 | 37 | | | 0.38 |
| 11 | 1.8 | >5 | ≈30 | 0.094 |
| 12 | 0.84 | 2.0 | 31 | 0.10 |
| 13 | 0.22 | 1.9 | >30 | 0.21 |
| 14 | >100 | >5 | >30 | 0.29 |

In Table I the pharmacological data of the compounds 1-9 prepared by us are compared with the results of compounds 11-14 previously described in the Prior Art. The data of table I above show that the methylpyridines 2, 4 and 5 are potent antihistamines, with stronger activity than the 4-pyridine 11 and the compounds 12–14, which have a carbonyl group attached to the piperidine ring. It is remarkable the activity of compound 4, which is 20-fold more potent than compound 11 and 25- to 70-fold more potent than compounds 12–14. These results show that antihistaminic activity is highly dependent on the precise nature and position of the substituent in the pyridine. In effect, it is surprising and totally unexpected that changes in the location of the methyl group result in such important changes in the antihistaminic activity. Thus, 5-methyl derivative 4 is aproximately a 100-fold more potent antihistamine than the corresponding 2-methyl derivative 3 and 10-fold more potent antihistamine than the corresponding 6-methyl and 4-methyl derivatives 2 and 5. It is demonstrated, therefore, that the precise location and nature of the substituents in compound 4 is optimal and unchangeable. It would not have been possible to a person skilled in the art to anticipate the improved activity of 4 in view of the activities of the structurally related prior art compounds.

PAF antagonistic acitvity is also very dependent on the substitution of the pyridine ring. In general, both the compounds we have studied and the Prior Art compounds show poor activities, specially in the PAF-induced mortality test where the compounds are administered orally. The only exception is compound 4 which surprisingly exhibits a strong activity in this pharmacological test which is 10- or more fold superior to all the other tested compounds. Therefore, with compound 4, which is the object of the present invention, it has been possible to combine in the same molecule strong antihistaminic and PAF antagonistic activities, which makes the compound of the present invention particularly useful for the treatment of those disorders where cellular mediators such as PAF and histamine play an important role, for example asthma and allergic disorders.

According to the activity of compound 4, the present invention further provides compositions that contain the compound of the present invention, together with an excipient and optionally other auxiliary agents, if necessary. The compound of the present invention can be administered in different pharmaceutical formulation, the precise nature of which, as it is well known, will depend upon the chosen route of administration and the nature of the pathology to be treated.

Thus, solid compositions according to the present invention for oral administration include compressed tablets, dispersible powders, granules and capsules. In tablets, the active component is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are possible wherein the active ingredient is mixed with water or an oil medium, for example peanut oil, liquid paraffin or olive oil.

Dispersible powders and granules suitable for preparation of a suspension by the addition of water provide the active ingredient in admixture with a dispersing or wetting agent, a suspending agent, such as sodium carboxymethylcellulose, sodium alginate, polyvinylpirrolidone, gum tragacanth, xantham gum, gum acacia, and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods. The spray compositions will contain a suitable propellent.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, the Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

The compound of the invention may also administered in the form of suppositories for rectal administration of the drug, or as creams, ointments jellies, solutions or suspensions for topical use and pessaries for vaginal administration.

The compound of the invention may also be deliverable transdermally. The transdermal compositions include creams, lotions, aerosols and/or emulsions and can be included in a conventional transdermal patch of the matrix or reservoir type.

The dosage and frequency of dose may vary depending upon symptoms, age and body weight of the patient, as well as upon the route of administration, but, in general, the compound of the present invention may be administered orally in a daily dose of from 1–500 mg for an adult, preferably a dosage from 5–100 mg, which may be administered either as a single dose or as divided doses. A preferred dosage for human patients is from 0.01 to 5 mg/Kg of body weight, more preferably from 0.05 to 1 mg/Kg of body weight.

Following are some representative preparations for tablets, capsules, syrups, aerosols and injectables. They can be prepared following standard procedures and they are useful in the treatment of the diseases where PAF and/or histamine are involved.

| Tablets | |
|---|---|
| Compound 4 | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound 4 | 100 mg |
| Lactose | 197 mg |
| Magnesium stearate | 3 mg |
| | 300 mg |
| Syrup | |
| Compound 4 | 0.4 g |
| Sucrose | 45 g |
| Flavoring agent | 0.2 g |
| Sweetening agent | 0.1 g |
| Water to | 100 mL |
| Aerosol | |
| Compound 4 | 4 g |
| Flavoring agent | 0.2 g |
| Propylene glycol to | 100 mL |
| Suitable propellent to | 1 unit |
| Injectable preparation | |
| Compound 4 | 100 mg |
| Benzylic alcohol | 0.05 mL |
| Propylene glycol | 1 mL |
| Water to | 5 mL |

The following examples further illustrate the invention:

PREPARATION 1

8-chloro-11-(4-piperidyliden)-6,11-dihydro-5H-benzo[5,6]cyclohepta [1,2-b]pyridine To a solution of 9.1 g (0.238 mol) of loratadine in 120 mL of dry chloroform, was added 7.5 mL of trimethylsilyl iodide. Then, the mixture was heated to 55°-60° C. under an argon atmosphere overnight. 30 mL of 0.5N HCl was added and the mixture was stirred for some time more. After basifying with NaOH, the resulting solution was extracted with chloroform (2-3 times). The organic phase was dried over sodium sulfate and the solvent was removed, to yield 12.89 g of a residue that was purified by crystallization in acetonitrile. 5.69 g of the desired product was obtained (yield: 77%).

mp: 154°-155° C.;

$^1$H RMN (80 MHz, CDCl$_3$) δ (TMS): 8.39 (d, J=3.5 Hz, 1H, ar), 7.43 (d, J=7.6 Hz, 1H, ar), 7.13 (m, 4H, ar), 3.5-2.2 (m, 12H), 1.86 (s, 1H, NH).

EXAMPLE 1

8-chloro-11-(1-(3-pyridylmethyl)-4-piperidyliden)-6,11-dihydro-5H-benzo[5,6]cyclohepta[1,2-b]pyridine To a solution of 0.4 g (1.3 mmol) of the product obtained in preparation 1 in 5 mL of anhydrous CHCl$_3$, was added 0.2 mL (1.56 mmol) of triethylamine. The resulting mixture was cooled (ice bath), 0.25 g (1.5 mmol) of 3-(chloromethyl)pyridine monohydrochloride was added and the mixture was stirred at room temperature under an argon atmosphere overnight. After diluting with CHCl$_3$, the solution was washed with 0.1N NaOH and the aqueous phase was extracted again with CHCl$_3$. The organic phase was dried over sodium sulfate and the solvent was removed, to afford 0.73 g of a residue that was chromatographed on silica gel (chloroform:methanol:ammonia, 60:2:0.2). 0.3 g of the title compound of the example was obtained (yield: 57%).

mp: 115.2° C.;

$^1$H RMN (80 MHz, CDCl$_3$) δ (TMS): 8.5 (m, 2H, ar), 8.4 (d, J=5.2 Hz, 1H, ar), 7.7 (d, J=8.8 Hz, 1H, ar), 7.45 (dd, Ja=8.8 Hz, Jb=2.2 Hz, 1H, ar), 7.28 (m, 1H, ar), 7.12 (m, 4H), 3.46 (m, 6H), 3.0-2.1 (m, 8H).

EXAMPLE 2

8-chloro-11-(1-[(6-methyl-3-pyridyl)metyl]-4-piperidyliden)-6,11-dihydro-5H-benzo[5,6]cyclohepta[1,2-b]pyridine Following the procedure described in example 1, but using 6-methyl-3-(chloromethyl)pyridine instead of 3-(chloromethyl)pyridine, the title compound of this example was obtained as the free base (yield: 84%).

IR (KBr) ν: 3033, 2914, 2798, 1597, 1560, 1474, 1433, 1337, 1292, 1114, 989, 830, 733 cm$^{-1}$;

$^1$H RMN (80 MHz, CDCl$_3$) δ (TMS): 8.38 (d, J=2.6 Hz, 2H, ar), 7.56 (dd, J$_a$=8.2 Hz, J$_b$=2 Hz, 1H, ar), 7.41 (dd, J$_a$=7.8 Hz, J$_b$=1.5 Hz, 1H, ar), 7.12 (m, 5H, ar), 3,47 (s, 2H, CH$_2$N), 3.3 (m, 2H), 3.0-2.1 (m, 13H).

EXAMPLE 3

8-chloro-11-(1-[(2-methyl-3-pyridyl)methyl]-4-piperidyliden)-6,11-dihydro-5H-benzo[5,6]cyclohepta[1,2-b]pyridine Following the procedure described in example 1, but using 2-methyl-3-(chloromethyl)pyridine instead of 3-(chloromethyl)pyridine, the title compound of this example was obtained (yield: 30%).

mp: 81.4°-87.2° C.;

IR (KBr) ν: 3045, 2913, 2793, 1581, 1472, 1434, 1360, 1294, 1114, 828, 785, 729 cm$^{-1}$;

$^1$H RMN (80 MHz, CDCl$_3$) δ (TMS): 8.36 (m, 2H, ar), 7.59 (dd, J$_a$=7.6 Hz, J$_b$=1.4 Hz, 1H, ar), 7.42 (dd, J$_a$=7.3 Hz, J$_b$=1.5 Hz, 1H, ar), 7.13 (m, 5H, ar), 3.45 (s, 2H, CH$_2$N), 3.35 (m, 2H), 3.0-2.2 (m, 13H).

EXAMPLE 4

8-chloro-11-(1-[(5-methyl-3-pyridyl)methyl]-4-piperidyliden)-6,11-dihydro-5H-benzo[5,6]cyclohepta[1,2-b]pyridine To a solution of 1.7 mL (15 mmol) of 3,5-lutidine in 100 mL of CCl$_4$ was added 2.6 g (15 mmol) of NBS and the mixture was stirred at reflux under an argon atmosphere for 2 h. Then, the mixture was allowed to cool, the solid obtained was filtered off and to the filtrate was added 2.4 g (7.5 mmol) of the compound obtained in preparation 1 and 20 mg of 4-(dimethylamino)pyridine. The resulting mixture was stirred at room temperature for 18 h and 1.68 mL of triethylamine was added. It was diluted with 100 mL of dichloromethane and washed with 0.5N NaHCO$_3$ solution and with water. The organic phase was dried over sodium sulfate and the solvent was removed, to give 5.7 g of a residue that was chromatographed on silica gel (chloroform:methanol:ammonia, 60:2:0.2). 1.3 g of the title compound of the example was obtained as a white solid (yield: 40%).

mp: 58°-61° C.;

IR (KBr) ν: 3419, 3014, 1635, 1576, 1472 cm$^{-1}$;

$^1$H RMN (80 MHz, CDCl$_3$) δ (TMS): 8.39 (m, 3H, ar), 7.48 (m, 1H, ar), 7.37 (m, 1H, ar), 7.12 (m, 4H, ar), 3.45 (s, 2H, CH$_2$N), 3.36 (m, 2H), 3.1-2.1 (m, 13H).

$^{13}$C RMN (20.15 MHz, CDCl$_3$) δ (TMS): 157.20 (C), 148.93 (CH), 147.46 (CH), 146.48 (CH), 139.50 (C), 138.56 (C), 137.06 (CH), 133.3 (C), 132.54 (C), 130.67 (CH), 128.80 (CH), 125.85 (CH), 121.92 (CH), 59.84 (CH$_2$), 54.63 (CH$_2$), 31.70 (CH$_2$), 31.32 (CH$_2$), 30.80 (CH$_2$), 30.56 (CH$_2$), 18.14 (CH$_3$).

EXAMPLE 5

8-chloro-11-(1-[(4-methyl-3-pyridyl)methyl]-4-piperidyliden)-6,11-dihydro-5H-benzo[5,6]cyclohepta[1,2-b]pyridine Following the procedure described in example 4, but using 3-(bromomethyl)-4-methylpyridine instead of 3-(bromomethyl)-5-methylpyridine, the title compound of this example was obtained (yield: 14%).

mp: 95.5°–100.8° C.;

IR (KBr) v: 2914, 1630, 1587, 1472, 1432, 1113, 990, 828, 751 cm$^{-1}$;

$^1$H RMN (80 MHz, CDCl$_3$) δ (TMS): 8.36 (m, 3H, ar), 7.5-7.0 (m, 6H, ar), 3.45 (s, 2H, CH$_2$N), 3.27 (m, 2H), 3.0-2.1 (m, 13H).

EXAMPLE 6

8-chloro-11-(1-[(2-chloro-3-pyridyl)methyl]-4-piperidyliden)-6,11-dihydro-5H-benzo[5,6]cyclohepta[1,2-b]pyridine Following the procedure described in example 1, but using 2-chloro-3-(chloromethyl)pyridine instead of 3-(chloromethyl)pyridine, the title compound of this example was obtained (yield: 38%).

mp: 56.6°–60.2° C.;

IR (KBr) v: 3038, 2893, 2790, 1574, 1555, 1432, 1405, 1337, 1112, 1063, 989, 828, 788 cm$^{-1}$;

$^1$H RMN (80 MHz, CDCl$_3$) δ (TMS): 8.40 (dd, J$_a$=5.3 Hz, J$_b$=2 Hz, 1H, ar), 8.29 (dd, J$_a$=5.3 Hz, J$_b$=2 Hz, 1H, ar), 7.92 (dd, J$_a$=8 Hz, J$_b$=2 Hz, 1H, ar), 7.46 (dd, J$_a$=8 Hz, J$_b$=2 Hz, 1H, ar), 7.13 (m, 5H, ar), 3.60 (s, 2H, CH$_2$N), 3.4 (m, 2H), 3.1-2.2 (m, 10H).

EXAMPLE 7

8-chloro-11-(1-[(6-chloro-3-pyridyl)methyl]-4-piperidyliden)-6,11-dihydro-5H-benzo[5,6]cyclohepta[1,2-b]pyridine Following the procedure described in example 1, but using 6-chloro-3-(chloromethyl)pyridine instead of 3-(chloromethyl)pyridine, the title compound of this example was obtained (yield: 15%).

mp: 76.2°–81.7° C.;

$^1$H RMN (80 MHz, CDCl$_3$) δ (TMS): 8.38 (dd, J$_a$=4.8 Hz, J$_b$=1.7 Hz, 1H, ar), 8.28 (d, J=2.3 Hz, 1H, ar), 7.66 (dd, J$_a$=7.2 Hz, J$_b$=2.4 Hz, 1H, ar), 7.46 (dd, J$_a$7.2 Hz, J$_b$=1.4 Hz, 1H, ar), 7.12 (m, 5H, ar), 3.47 (s, 2H, CH$_2$N), 3.33 (m, 2H), 3.0-2.1 (m, 10H).

EXAMPLE 8

8-chloro-11-(1-[(3-bromo-5-pyridyl)methyl]-4-piperidyliden)-6,11-dihydro-5H-benzo[5,6]cyclohepta[1,2-b]pyridine, trihydrochloride a)
8-chloro-11-(1-[(3-bromo-5-pyridyl)carbonyl]-4-piperidyliden)-6,11-dihydro-5H-benzo[5,6]cyclohepta[1,2-b]pyridine To a mixture of 1.2 g (3.86 mmol) of the product obtained in preparation 1, 0.8 g (4 mmol) of 5-bromonicotinic acid and 0.54 g (4 mmol) of 1-hydroxybenzotriazole solved in 10 mL of dimethylformamide, was added 0.82 g (4 mmol) of dicyclohexylcarbodiimide and the resulting solution was stirred at room temperature under an argon atmosphere overnight. The solvent was removed under vacuum, the residue was stirred with ethyl acetate and the white solid formed was filtered off. The organic solution was washed with a saturated solution of sodium bicarbonate, with water and finally with a saturated solution of sodium chloride. The organic phase was dried over sodium sulfate and the solvent was removed, to afford 2.3 g of a crude that was chromatographed on silica gel (chloroform:methanol, 5%). 1.75 g of the desired product was obtained (yield: 92%).

mp: 87.5°–96.4° C.;

IR (KBr) v: 3035, 2990, 2919, 1631, 1433, 1417, 1276, 1242, 991, 752 cm$^{-1}$;

$^1$H RMN (80 MHz, CDCl$_3$) δ (TMS): 8.60 (d, J=2 Hz, 1H, ar), 8.57 (d, J=1.6 Hz, 1H, ar), 8.40 (m, 1H, ar), 7.90 (m, 1H, ar), 7.48 (d, J=7.7Hz, 1H, ar), 7.14 (m, 4H, ar), 3.36 (m, 4H), 3.0-2.3 (m, 8H).

b) Title compound of the example

To a solution of 0.12 g (3.2 mmol) of LiAlH$_4$ in 5 mL of anhydrous tetrahydrofuran, cooled with an ice bath, was added dropwise 0.84 g (1.7 mmol) of the product obtained in example 8a. The resulting mixture was stirred under an argon atmosphere at room temperature overnight and then in the refrigerator one night more. It was placed in an ice bath and 0.17 mL of water and 0.35 mL of tetrahydrofuran was added; subsequently was added 0.17 mL of 15% NaOH solution and 0.46 mL of water. The precipitate formed was filtered and after washing with tetrahydrofuran, the solvent was removed. Some chloroform was added, the organic phase was dried over sodium sulfate and the solvent was removed, to afford a residue that was chromatographed on silica gel (chloroform:methanol, 3%). 0.22 g of the title compound of this example was obtained (yield: 27%).

mp: 55.0°–62.2° C.;

IR (KBr) v: 3032, 2934, 2792, 1577, 1473, 1432, 1416, 1360, 1114, 1021, 828, 753 cm$^{-1}$;

$^1$H RMN (80 MHz, CDCl$_3$) δ (TMS): 8.55 (d, J=1.5 Hz, 1H, ar), 8.39 (m, 2H, ar), 7.86 (s, 1H, ar), 7.42 (d, J=7.5 Hz, 1H, ar), 7.12 (m, 4H, ar), 3.49 (m, 2H, CH$_2$N), 3.36 (m, 2H), 3.0-2.1 (m, 10H).

EXAMPLE 9

8-chloro-11-(1-[(6-methoxy-3-pyridyl)methyl]-4-piperidyliden)-6,11-dihydro-5H-benzo[5,6]cyclohepta[1,2-b ]pyridine Following the procedure described in example 1, but using 3-(chloromethyl)-6-methoxypyridine instead of 3-(chloromethyl)pyridine, the title compound of this example was obtained (yield: 21%).

mp: 60.2°–64.1° C.;

IR (KBr) v: 2934, 2893, 1603, 1487, 1432, 1285, 1268, 1115, 1025, 830 cm$^{-1}$;

$^1$H RMN (80 MHz, CDCl$_3$) δ (TMS): 8.38 (dd, J$_a$=4 Hz, J$_b$=1.6 Hz, 1H, ar), 8.02 (d, J=2.1 Hz, 1H, ar), 7.57 (dd, J$_a$=8.5 Hz, J$_b$=2.4 Hz, 1H, ar), 7.42 (dd, J$_a$=8 Hz, J$_b$=1.5 Hz, 1H, ar), 7.12 (m, 4H, ar), 6.69 (d, J=8.5 Hz, 1H, ar), 3.92 (s, 3H, OCH$_3$), 3.43 (s, 2H, CH$_2$N), 3.33 (m, 2H), 3.0-2.1 (m, 10H).

EXAMPLE 10

8-chloro-11-(1-[(5-methyl-3-pyridyl)methyl]-4-piperidyliden)-6,11-dihydro-5H-benzo[5,6]cyclohepta[1,2-b]pyridine, trihydrochloride To a cooled (0° C.) solution of 1.13 g of the compound obtained in example 4 in ethyl acetate, was added a diethyl ether solution saturated with hydrochloric acid gas, to give the title compound of this example as a white solid (yield: 80%).

mp: 213°–217° C. ($C_{26}H_{26}ClN_3.3HCl$).

EXAMPLE 11

8-chloro-11-(1-[(5-methyl-3-pyridyl)methyl]-4-piperidyliden)-6,11-dihydro-5H-benzo[5,6]cyclohepta[1,2-b]pyridine, hemipentafumarate To a solution of 3 g (7.2 mmol) of the product obtained in example 4 in 15 mL of AcOEt was added a solution of 2.5 g (21.6 mmol) of fumaric acid dissolved in 17 mL of MeOH. After cooling in the freezer for 12 h, the solid formed was filtered (4.12 g, 81%).

mp: 168°–169° C. ($C_{26}H_{26}ClN_3.2.5\ (CHCOOH)_2$);

$^1$H RMN (80 MHz, CDCl$_3$) δ (TMS): 8.36 (m, 3H, ar), 7.79 (m, 1H, ar), 7.58 (m, 1H, ar), 7.12 (m, 4H, ar), 6.80 (s, 5H, CH=CH), 4.81 (s, 5H, H+), 4.08 (s, 2H, CH$_2$N), 3.6-2.4 (m, 12H), 2.38 (s, 3H).

EXAMPLE 12

8-chloro-11-(1-[(5-methyl-3-pyridyl)methyl]-4-piperidyliden)-6,11-dihydro-5H-benzo[5,6]cyclohepta[1,2-b]pyridine, dioxalate To a solution of 0.7 g (1.7 mmol) of the product obtained in example 4 in 3 mL of AcOEt was added a solution of 0.31 g (3.4 mmol) of oxalic acid dissolved in 2 mL of AcOEt. After cooling in the freezer for 12 h, the solid formed was filtered (0.9 g, 90%).

mp: 140°–146° C. ($C_{26}H_{26}ClN_3.2\ (COOH)_2$).

EXAMPLE 13

8-chloro-11-(1-[(5-methyl-3-pyridyl)methyl]-4-piperidyliden)-6,11-dihydro-5H-benzo[5,6]cyclohepta[1,2-b]pyridine, hemitricitrate To a solution of 0.7 g (1.7 mmol) of the product obtained in example 4 in 3 mL of AcOEt was added a solution of 0.52 g (2.5 mmol) of citric acid monohydrate dissolved in 4 mL of MeOH. After cooling in the freezer for 12 h the solid formed was filtered (0.24 g, 20%).

mp: 83°–91° C. ($C_{26}H_{26}ClN_3.1.5\ C_6H_8O_7$).

We claim:

1. 8-chloro-11-[1-[(5-methyl-3-pyridyl)methyl]-4-piperidyliden]-6,11-dihydro-5H-benzo[5,6]cyclohepta[1,2-b]pyridine or a pharmaceutically acceptable salt or solvate thereof.

2. A pharmaceutical composition which comprises an effective amount of 8-chloro-11-[1-[(5-methyl-3-pyridyl)methyl]-4-piperidyliden]-6,11-dihydro-5H-benzo[5,6]cyclohepta[1,2-b]pyridine or a pharmaceutically acceptable salt or solvate thereof in combination with a pharmaceutically acceptable excipient.

3. A method for treating asthma or allergic disorders in mammals, which comprises administering to the mammal in need thereof an effective amount of 8-chloro-11-[1-[(5-methyl-3-pyridyl)methyl]-4-piperidyliden]-6,11-dihydro-5H-benzo[5,6]cyclohepta[1,2-b]pyridine or a pharmaceutically acceptable salt or solvate thereof.

4. A method according to claim 3 wherein said pharmaceutically acceptable salt is a fumarate salt.

5. A pharmaceutical composition according to claim 2 wherein said pharmaceutically acceptable salt is a fumarate salt.

6. A compound according to claim 1 wherein said pharmaceutically acceptable salt is a fumarate salt.

* * * * *